US010736515B2

(12) United States Patent
Stoian et al.

(10) Patent No.: US 10,736,515 B2
(45) Date of Patent: Aug. 11, 2020

(54) PORTABLE MONITORING DEVICE FOR BREATH DETECTION

(71) Applicant: Clarkson University, Potsdam, NY (US)

(72) Inventors: Alexandru B Stoian, Potsdam, NY (US); James J. Carroll, Potsdam, NY (US); Daniel Jean Rissacher, Potsdam, NY (US)

(73) Assignee: Clarkson University, Potsdam, NY (US)

( * ) Notice: Subject to any disclaimer, the term of this patent is extended or adjusted under 35 U.S.C. 154(b) by 518 days.

(21) Appl. No.: 13/912,694

(22) Filed: Jun. 7, 2013

(65) Prior Publication Data

US 2013/0331662 A1 Dec. 12, 2013

Related U.S. Application Data

(60) Provisional application No. 61/656,545, filed on Jun. 7, 2012.

(51) Int. Cl.
*A61B 5/0205* (2006.01)
*A61B 7/00* (2006.01)
*A61B 5/00* (2006.01)
A61B 5/1455 (2006.01)

(52) U.S. Cl.
CPC .......... *A61B 5/0205* (2013.01); *A61B 5/0002* (2013.01); *A61B 7/003* (2013.01); *A61B 5/14551* (2013.01)

(58) Field of Classification Search
CPC ... A61B 5/0205; A61B 5/0002; A61B 5/0816; A61B 5/01; A61B 5/02055; A61B 5/0022; A61B 5/74; A61B 5/7405; A61B 5/742; A61B 5/7455; A61B 5/746; A61B 5/7465; A61B 5/7475; A61B 5/0024; A61B 5/024; A61B 7/003
USPC ....... 600/300, 301, 323, 344, 386, 391, 483, 600/529, 534, 586
See application file for complete search history.

(56) References Cited

U.S. PATENT DOCUMENTS

| 5,928,156 | A | 7/1999 | Krumbiegel et al. |
| 8,403,865 | B2 * | 3/2013 | Halperin ................ A61B 5/113 600/529 |
| 8,506,480 | B2 * | 8/2013 | Banet ................... A61B 5/0408 600/300 |

(Continued)

OTHER PUBLICATIONS

International Search Report Form PCT/ISA/220, International Application No. PCT/US2013/044728, pp. 1-6, dated Sep. 12, 2013.

*Primary Examiner* — Timothy J Neal
*Assistant Examiner* — William B Chou
(74) *Attorney, Agent, or Firm* — Bond Schoeneck & King, PLLC; George McGuire

(57) ABSTRACT

Methods, devices, and systems for monitoring a health parameter of a user. A portable monitoring device comprises a housing adapted to couple to a user proximate to the user's respiratory tract; a first audio sensor, disposed in the housing, is adapted to detect a breath sound of the user and create breath sound data; and a processor coupled to the first audio sensor transduces the breath sound data into a modified breath sound signal which is representative of a parameter of the user's breathing, and the processor is adapted to compare the parameter of the user's breathing to a predetermined parameter threshold.

16 Claims, 5 Drawing Sheets

(56) References Cited

U.S. PATENT DOCUMENTS

| | | | | |
|---|---|---|---|---|
| 8,920,343 B2 * | 12/2014 | Sabatino | .................. | A61B 7/00 |
| | | | | 381/67 |
| 2002/0097155 A1 | 7/2002 | Cassel et al. | | |
| 2006/0064037 A1 * | 3/2006 | Shalon | .................. | A61B 5/0006 |
| | | | | 600/586 |
| 2006/0069319 A1 | 3/2006 | Elhag | | |
| 2006/0282131 A1 * | 12/2006 | Caparso | ............... | A61N 1/3601 |
| | | | | 607/62 |
| 2008/0269625 A1 * | 10/2008 | Halperin | ................. | A61B 5/113 |
| | | | | 600/508 |
| 2008/0306367 A1 | 12/2008 | Koehler et al. | | |
| 2009/0024004 A1 | 1/2009 | Yang | | |
| 2010/0083968 A1 * | 4/2010 | Wondka | ................ | A61M 16/12 |
| | | | | 128/204.23 |
| 2010/0305418 A1 * | 12/2010 | Deliwala | ............ | A61B 5/14551 |
| | | | | 600/324 |
| 2011/0125060 A1 * | 5/2011 | Telfort | ................... | A61B 7/003 |
| | | | | 600/586 |
| 2011/0213273 A1 * | 9/2011 | Telfort | ................... | A61B 7/003 |
| | | | | 600/586 |
| 2012/0302846 A1 * | 11/2012 | Volmer | .............. | A61B 5/02416 |
| | | | | 600/324 |
| 2013/0218582 A1 * | 8/2013 | LaLonde | ................ | A61B 5/686 |
| | | | | 705/2 |
| 2014/0228721 A1 * | 8/2014 | Ehrenreich | ........ | A61H 23/0245 |
| | | | | 601/47 |
| 2015/0031964 A1 * | 1/2015 | Bly | ........................ | G16H 40/67 |
| | | | | 600/301 |
| 2015/0137988 A1 * | 5/2015 | Gravenstein | ........... | A61B 5/002 |
| | | | | 340/870.02 |
| 2016/0150978 A1 * | 6/2016 | Yuen | .................... | A61B 5/0205 |
| | | | | 600/301 |
| 2016/0367779 A1 * | 12/2016 | Landis | ................ | A61M 16/049 |

\* cited by examiner

PORTABLE MONITORING DEVICE FOR BREATH DETECTION

CROSS-REFERENCE TO RELATED APPLICATIONS

This application claims priority to U.S. Provisional Patent Application Ser. No. 61/656,545, filed on Jun. 7, 2012 and entitled "Breath Monitor," the entire disclosure of which is incorporated herein by reference.

BACKGROUND OF THE INVENTION

1. Field of the Invention

The present invention relates to medical diagnostic instruments, home-use physiological instruments, and sports-medicine physiological instruments.

2. Description of the Related Art

In many applications it is desirable to monitor an individual's cardiopulmonary system to determine current condition. Respiratory function, for example, can be monitored by the rate of respiration, by the length, volume, and/or strength of inhalation or exhalation, and by audible variations in breath sounds and/or frequencies over time or space.

In the past, respiration rates have been monitored using breathing belts applied around the chest or abdomen and by respiration sensors placed in front of the mouth and/or nose. Measuring the length of inhalation and exhalation can utilize similar devices with the length of breath being applied to algorithms which estimate volume or strength of inhalation/exhalation. Flow meters can also be applied to more accurately measure the volume and strength of breath. Audible variations in breath sounds are commonly observed through the use of a stethoscope by listening to changes in tone (audio wavelength) over time, and changing the position of the stethoscope to observe changes over space.

Generally, the cardiopulmonary system's overall ability to deliver oxygen to the body is monitored using a pulse oximeter which typically measures the absorption of red and infrared light through a patient's tissue to determine oxygen saturation ($SpO_2$) level. A pulse oximeter generally comprises at least one red light source and one infrared light source with a corresponding detector for each. The orientation of the source and detector can either be on opposing sides of the tissue (transmittance) or on the same surface (reflectance). De-oxyhemoglobin (RHb) absorbs more red light than oxyhemoglobin ($HbO_2$) and oxyhemoglobin absorbs more infrared light than de-oxyhemoglobin. Thus using this known relationship the oxygen saturation can be calculated. In addition, the absorption varies as blood vessels expand and contract allowing a pulse oximeter to also measure heart rate.

However, respiratory monitoring devices have traditionally been both bulky and expensive. These devices cannot easily be used by a user outside of a hospital setting, and certainly cannot be worn by the user as she performs her normal daily routine. Accordingly, there is a continued need for monitoring multiple pulmonary functions and parameters using a single lightweight wearable device.

BRIEF SUMMARY OF THE INVENTION

A primary objective is to use one or more microphones to monitor breathing together with a pulse oximeter to monitor oxygen saturation and heart rate on an integrated, long-duration wearable device that can be used during normal daily activities as well as in hospital and research settings. The user may be a medical professional, researcher or the subject wearing the device.

A further objective is to allow data collected by the portable monitoring device to be wirelessly transmitted, thereby allowing recording and/or monitoring of both real-time and recorded vital sign, parameters, and raw data (e.g., breath sounds) on, for example, computers, handheld devices, or remotely over a telecommunication network such as the Internet, an intranet, or telephone connection.

Another objective is to include patient notification programming and/or systems into the device, which may include for example tactile stimulation, audio alerts, electrical stimulation, or combinations thereof. Similarly, the device could include programming and/or systems to notify a monitoring entity other than the patient himself of a predetermined or preprogrammed parameter, condition, or vital sign. The monitoring entity could be, for example, a physician or a monitoring company authorized to monitor the patient.

A further objective is to record data internally thereby allowing for periodic transfer of recorded information using a wireless and/or wired connection. Continuous transfer using a wireless connection is also possible.

An additional objective is to allow for a wide range of users and applications. The device could be used by any individual wishing to monitor cardiopulmonary functions or parameters. In addition, the device could be used by health care professionals or researchers to monitor cardiopulmonary functions or parameters during daily activities at any location (i.e., at home, in a clinic, at a hospital, etc.) with the ability to record and download data, real-time remote monitoring, automatic alerts to the patient, researcher and/or health care professional based on selectable conditions, remote review of recorded data and/or flagged events, and, through the use of pattern recognition algorithms, the ability to automatically detect certain health conditions. Furthermore, the device can be used in sports-medicine applications to assist athletes and professionals in optimization of activities and breath control.

According to one embodiment is a device adapted to be adhered, engaged, or otherwise affixed on or adjacent to a user's chest or neck for a period of time ranging from hours to days, and which incorporates one or more subcomponents used to provide breath sound monitoring, oxygen saturation, and heart rate. According to an embodiment the device includes support circuitry, a power supply, data storage, a patient alarm, and wired and/or wireless connectivity for offboard communication. Sound monitoring can be conducted using single or multiple microphones. In the case of multiple microphones, for example, one or more may be mounted against the chest or neck (proximal) for breath sound acquisition while one or more may be mounted on the distal side of the device to collect non-breath sources for noise cancellation capabilities. Oxygen saturation and pulse data can be acquired using a pulse oximeter mounted on the proximal side of the device. The data can be captured via data acquisition circuitry in the device which can then be processed for metric calculation and pattern recognition either by onboard circuitry or offboard through wired or wireless two-way connections. According to an embodiment a patient alarm is provided by an audio alarm or tactile (vibratory and/or electrostimulating) components. According to an embodiment the offboard connectivity, particularly wireless connectivity, is a significant capability as it allows off-board signal processing, thereby minimizing the size/power requirements of on-board processors, and also allows for remote monitoring.

Embodiments of the present invention comprise portable monitoring devices and systems. According to one embodiment is a portable monitoring device comprising: (i) a housing adapted to couple to a user proximate to the user's respiratory tract; (ii) a first audio sensor, disposed in the housing, adapted to detect a breath sound of the user and create breath sound data; and (iii) a processor coupled to the first audio sensor, wherein the processor transduces the breath sound data into a modified breath sound signal which is representative of a parameter of the user's breathing, and further wherein the processor is adapted to compare the parameter of the user's breathing to a predetermined parameter threshold.

According to an aspect, the portable monitoring device comprises a second audio sensor disposed in the housing and coupled to the processor, that is adapted to detect ambient noise and to create ambient sound data, and the processor utilizes the ambient sound data to transduce the breath sound data into said modified breath sound signal.

According to an aspect, the portable monitoring device comprises a pulse oximetry sensor, coupled to the processor, adapted to detect a heart rate value and a blood oxygenation value.

According to another aspect, the portable monitoring device comprises a non-transitory data storage medium adapted to store at least a portion of said breath sound data and at least a portion of said ambient sound data.

According to yet another aspect, the portable monitoring device comprises a display, coupled to the processor, adapted to output data to the user.

According to an aspect, the parameter of the user's breathing is selected from the group consisting of inhalation frequency or quality, exhalation frequency or quality, breath volume, breath flow, breaths per minute, respiratory rhythmicity, respiratory plasticity and combinations thereof.

According to another aspect, the portable monitoring device comprises a battery.

According to an aspect, the portable monitoring device comprises a signal generator, coupled to the processor, adapted to generate a signal if said user's breathing exceeds said predetermined parameter threshold. The signal can be, for example, an audible or haptic signal.

According to an aspect, the portable monitoring device comprises a communications module, coupled to the processor, adapted to communicate data from the portable monitoring device. According to an embodiment, the communications module communicates data wired or wirelessly.

According to an aspect, the portable monitoring device comprises an adhesive adapted to adhere the portable monitoring device to the skin of the user.

According to an aspect, the portable monitoring device comprises a user interface, coupled to the processor, and adapted to receive an input from the user.

A second embodiment of a portable monitoring device comprises: (i) a housing adapted to couple to a user proximate to the user's respiratory tracts; (ii) a first audio sensor, disposed in the housing, adapted to detect a breath sound of the user and create breath sound data; (iii) a pulse oximetry sensor, disposed in the housing, adapted to detect a heart rate value and a blood oxygenation value; (iv) a processor coupled to the first audio sensor and the pulse oximetry sensor, wherein the processor transduces the breath sound data into a modified breath sound signal which is representative of a parameter of the user's breathing, and further wherein the processor is adapted to compare the parameter of the user's breathing to a predetermined parameter threshold; (vi) a non-transitory data storage medium adapted to store at least a portion of said breath sound data, at least a portion of said ambient sound data, said heart rate value, and said blood oxygenation value; (vii) a signal generator, coupled to the processor, adapted to generate a signal if said user's breathing exceeds said predetermined parameter threshold, or if said heart rate value or said blood oxygenation value exceeds a predetermined threshold; and (viii) a communications module, coupled to the processor, adapted to communicate data from the portable monitoring device.

According to an aspect, the portable monitoring device comprises a second audio sensor disposed in the housing and coupled to the processor, that is adapted to detect ambient noise and to create ambient sound data, and the processor utilizes the ambient sound data to transduce the breath sound data into a modified breath sound signal.

According to an aspect, the portable monitoring device comprises a display, coupled to the processor, adapted to output data to the user.

According to an aspect, the parameter of the user's breathing is selected from the group consisting of inhalation frequency or quality, exhalation frequency or quality, breath volume, breaths per minute, and combinations thereof. According to an embodiment, the communications module communicates data wirelessly.

According to an aspect, the portable monitoring device comprises an adhesive adapted to adhere the portable monitoring device to the skin of the user.

According to an aspect, the portable monitoring device comprises a user interface, coupled to the processor, and adapted to receive an input from the user.

A third embodiment comprises a method for monitoring a health parameter of a user, the method comprising the steps of: (i) providing a portable monitoring device, the device comprising: (a) a housing adapted to couple to the user proximate to the user's respiratory tracts; (b) a first audio sensor, disposed in the housing, adapted to detect a breath sound of the user and create breath sound data; (c) a processor coupled to the first audio sensor; (ii) transducing, using the processor, the breath sound data into a modified breath sound signal which is representative of a health parameter of a user; and (iii) comparing, using the processor, the health parameter of a user to a predetermined parameter threshold.

According to an aspect, the device according to this method further comprises a second audio sensor disposed in the housing and coupled to the processor, that is adapted to detect ambient noise and to create ambient sound, and the processor utilizes the ambient sound data to transduce the breath sound data into said modified breath sound signal.

According to an aspect, the device according to this method further comprises a signal generator coupled to the processor, and the method further comprises the step of generating a signal if said health parameter exceeds said predetermined parameter threshold.

According to an aspect, the device according to this method further comprises a communications module coupled to the processor, and the method further comprises the step of communicating data from the portable monitoring device.

The details of one or more embodiments are described below and in the accompanying drawings. Other objects and advantages will in part be obvious, and in part appear hereinafter.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
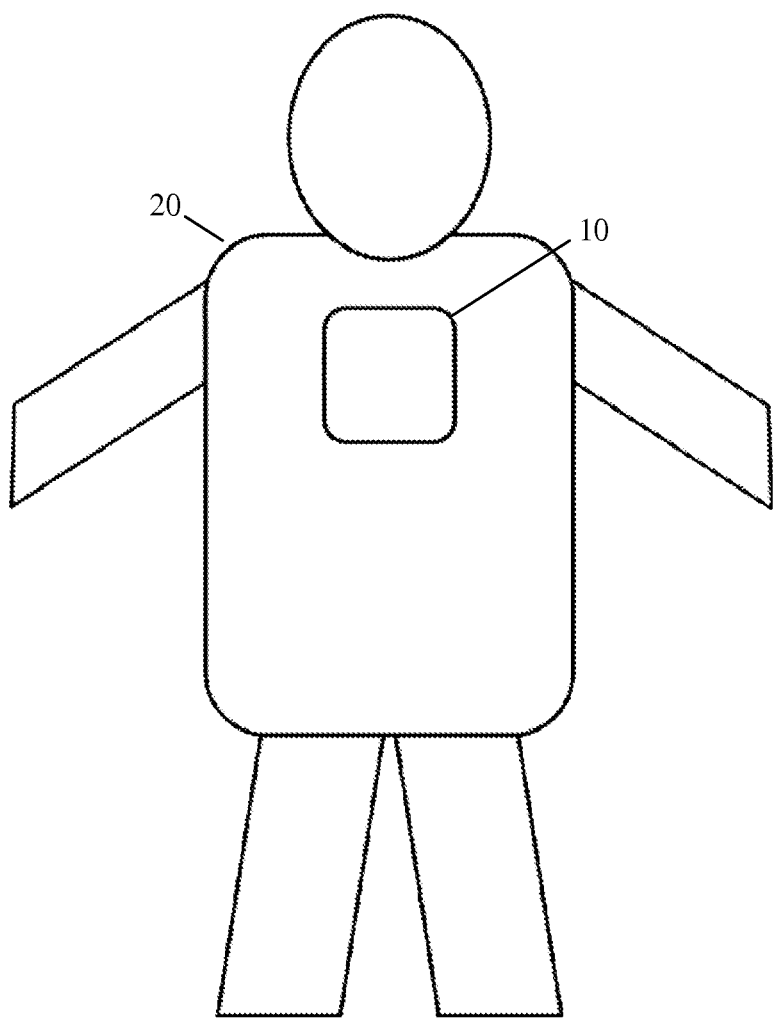
FIG. 1 is a schematic representation of a human body with placement of a portable monitoring device according to one embodiment.

Referring now to the drawings, wherein like reference numerals refer to like parts throughout, there is seen in FIG. 1 a portable monitoring device 10 that is placed on, near, or adjacent an airway, one or more lungs, or both (such as the neck or chest) of a user 20, according to one embodiment. Portable monitoring device 10 and user 20 are not shown to scale, and accordingly device 10 can be sized approximately as shown or can be miniaturized. Further, the shape of portable monitoring device 10 may be as shown, or, alternatively, the device can be any shape suitable to, for example, the needs of a user, a designer, or a manufacturer.

Figure 2:
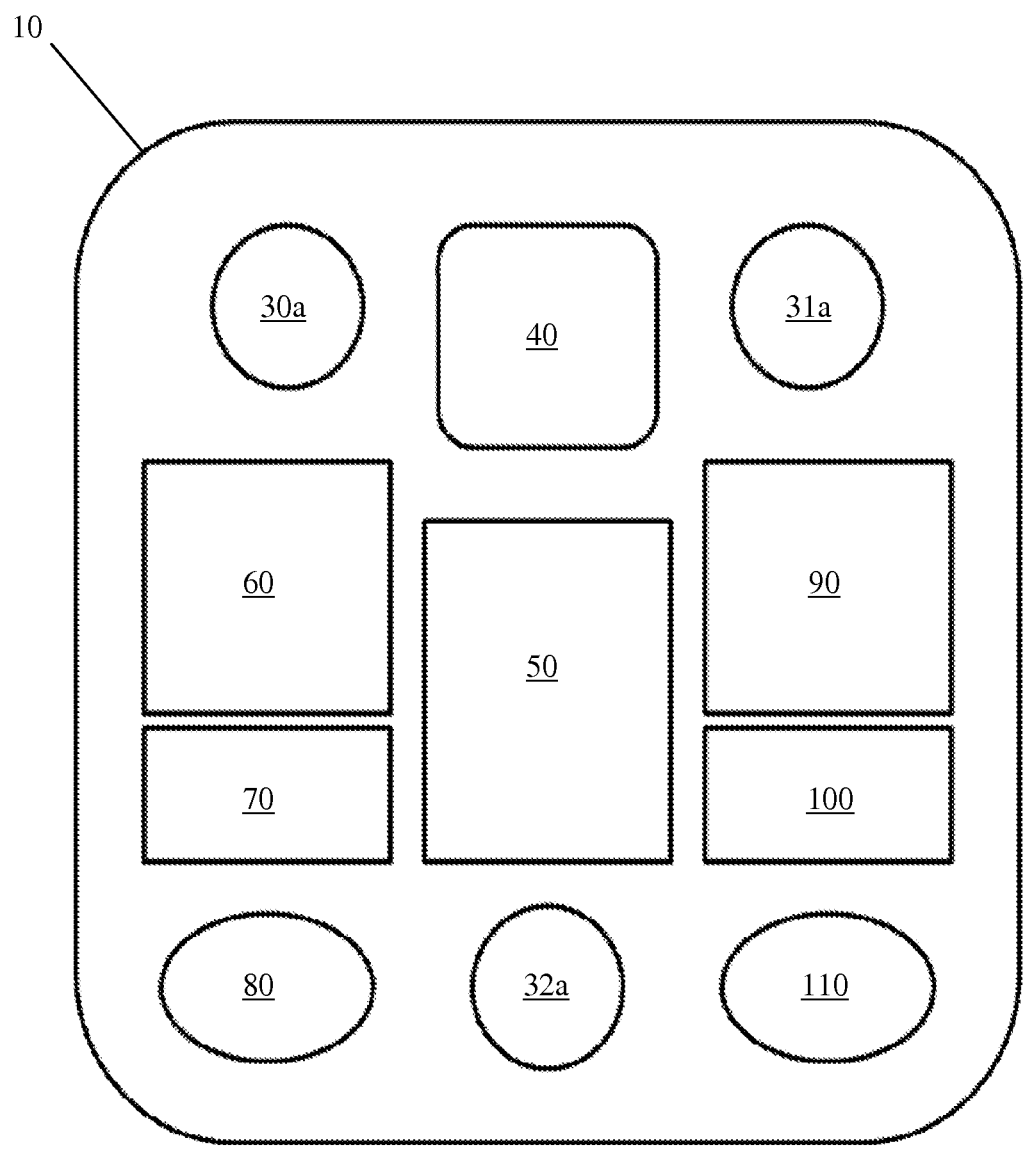
FIG. 2 is a schematic representation of a front view of a portable monitoring device according to one embodiment, including various subcomponents of the portable monitoring device.
Figure 3:
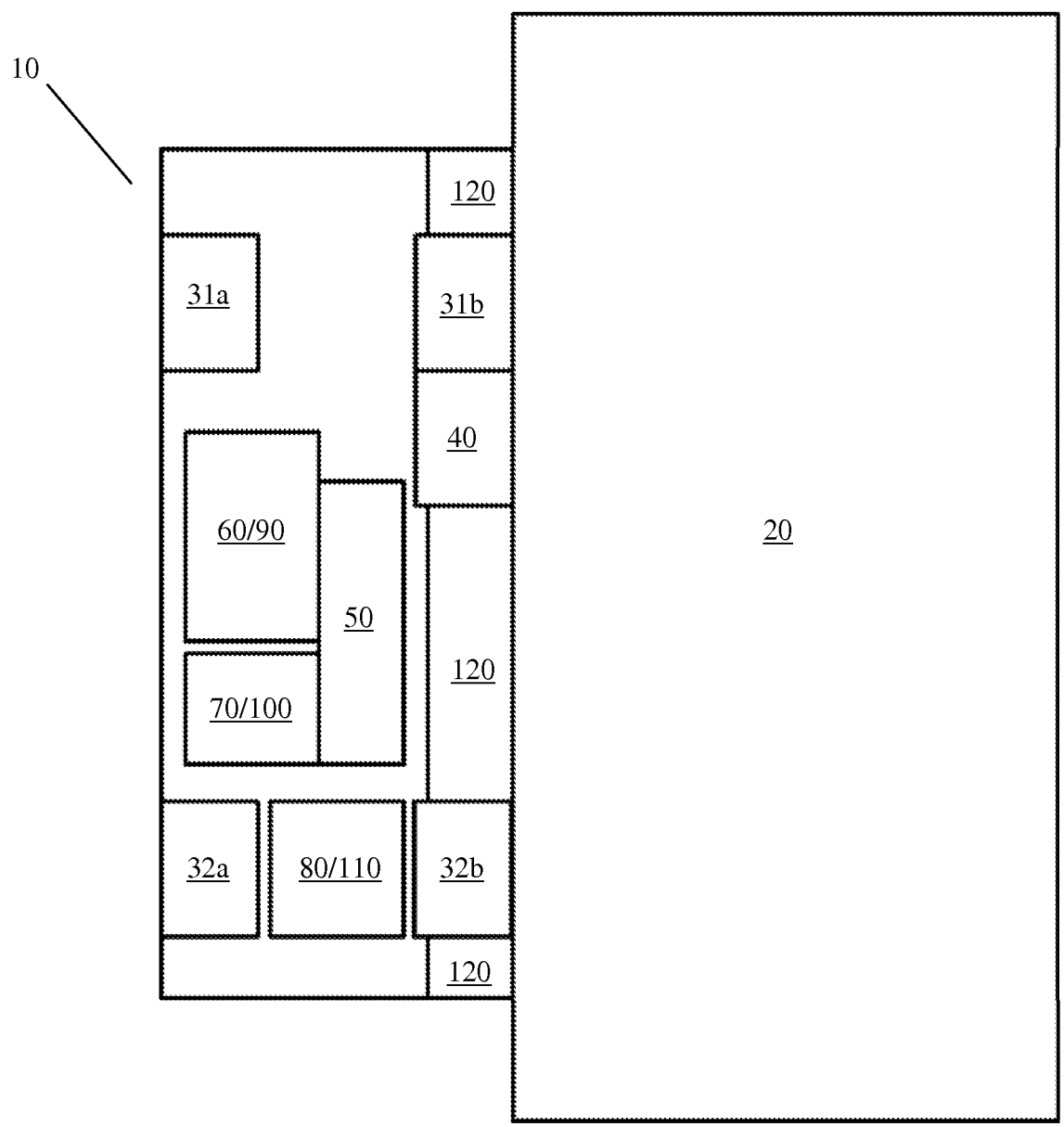
FIG. 3 is a schematic representation of a side view of a portable monitoring device according to one embodiment, including various subcomponents of the portable monitoring device.
Figure 4:
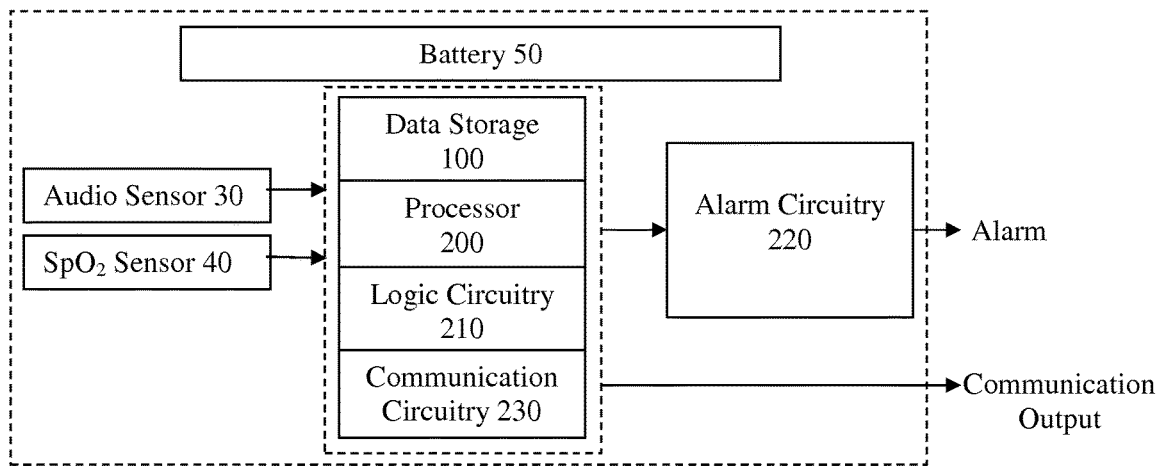
FIG. 4 is a block diagram representation of a portable monitoring device according to one embodiment.
Figure 5:
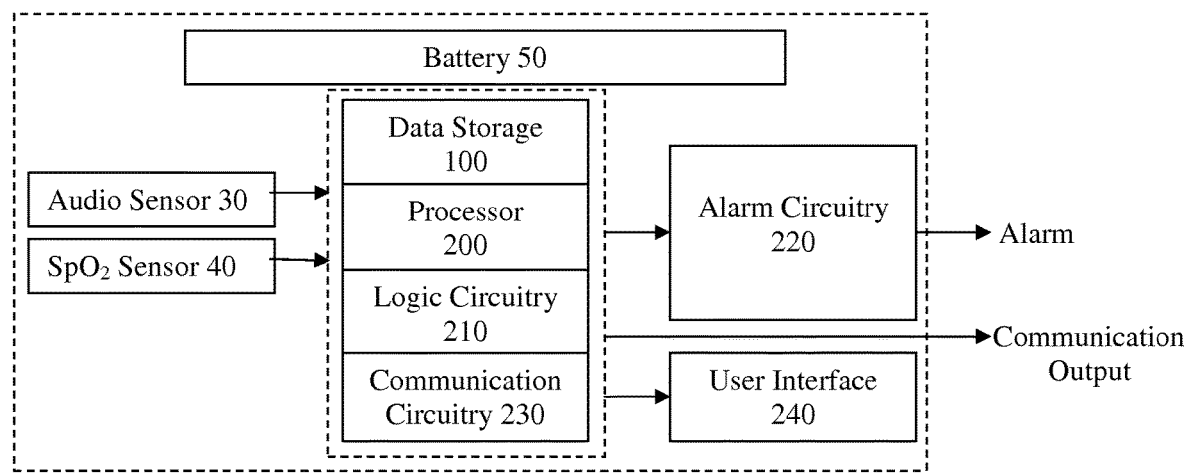
FIG. 5 is a block diagram representation of a portable monitoring device according to one embodiment including a user interface.

Portable monitoring device 10 comprises one or more sound detection and/or recording devices 30 utilized to monitor breathing. According to an embodiment, the device comprises a microphone 30 as shown in FIGS. 4 and 5. The microphone 30 can be situated on, near, or adjacent an airway, one or more lungs, or both (such as the neck or chest) of user 20. According to an embodiment, the device comprises three microphone pairs 30, 31, and 32, as depicted in FIGS. 2 and 3. For each microphone pair, one microphone can be situated in the device such that it is proximal/adjacent to the chest, airway, lung, or other portion of the breathing machinery in order to optimize the detection of internal physiological sounds (including but limited to breath and heart sounds), as shown in FIG. 3 (elements 30b (not shown), 31b, and 32b). The other member of the microphone pair can be situated in the device such that it is distal to the body in order to optimize the detection of exterior sounds (including but limited to movement noise, environmental background noise) (elements 30a (not shown), 31a, and 32a), as shown in both FIGS. 2 and 3. Although three microphone pairs are depicted in several of the figures, other variations are possible. For example, the device may comprise a single microphone, two or more non-paired microphones, a single microphone pair, or many microphone pairs.

According to an embodiment, audio data that has been captured by the one or more sound devices 30 is processed for analysis. Processing can occur immediately as the data is collected, can be queued briefly for processing, or can be stored and processed at a later date or time. For example, the audio data can be processed by an analog-to-digital converter so that digital processing methods can be applied. Conversion can be, for example, performed on a digital signal processing chip on device 10, a CPU on device 10, or the raw signal can be forwarded wirelessly for processing on another device (computer, phone, iPod, etc.).

The audio data can also be processed using first level algorithms meant to derive basic metrics such as those that are currently captured by other devices. Examples of first level algorithms would be inhale detection, exhale detection, breath volume and breath flow rate. According to an embodiment, inhale/exhale detection is done by taking a windowed Fourier transform of the data such that the magnitude of certain frequency bands are calculated for a specific window of time. The inhale or exhale sound has a unique frequency range (or pitch as in music) from other sounds captured such as talking that can be used for detection. Other processing methods include, for example, frequency techniques such as wavelets.

The processed audio data can also be further processed using second level algorithms that utilize the derived metrics in order to provide feedback on breathing to the user or physician. For example, a second level algorithm could be medical standard breathing measures such as breaths per minute or the Apnea-Hypopnia Index; or they could be a metric such as breathing quality, breath rhythmicity, plasticity, yawning, and other metrics. Any or all of these measures or metrics could be analyzed based on a time of day, a certain timeframe, or other time-related component. In addition to the above, second level algorithms could include feedback to the user when they are exhibiting poor breathing and should take a deep breath or some other breathing exercise, an interactive breathing exercise coach and feedback tool, or a daily tracker to give feedback on certain poor breathing times of day or events tied to poor breathing. An algorithm could also automatically detect any event that a physician currently diagnoses by listening to a stethoscope, such as a wheeze or stridor. Algorithms used to detect certain physiological states, breathing metrics or respiratory include those that are manually developed and automated pattern recognition techniques such as neural networks.

According to one embodiment, device 10 is a breathing monitor and regulator and a breathing volume and rhythmicity research tool. Device 10 monitors the rhythmicity of breathing and can warn the wearer when there are excessive episodes of apnea/hypopnea. According to an embodiment, the device utilizes the sounds generated by air movement captured by microphones, the oxygen saturation, and/or lung volumes recorded by stretching of chest bands or textile-like materials, among other potential properties. Accordingly, device 10 can alert the wearer when breathing is shallow or insufficient by decreased breathing which causes less oxygen availability to the body. This can lead to one or more of the following: (i) a switch in the metabolism to less aerobic and less fat based metabolism and increases craving for carbohydrates and chances of insulin resistance and diabetes, etc.; (b) decreased sports performance by faulty breathing; (c) inflammation through trigger of inflammatory hormones; (d) disease chance in general, in particular vascular and cancer. For research purposes, for example, circadian rhythm of respiration is influenced by sleep/wake state, stress, metabolic rate (and influences metabolic rate), medicines, alcohol and certain disease states, but it is presently insufficiently recognized and addressed in medical literature.

According to another embodiment, portable monitoring device 10 comprises a SpO$_2$ sensor 40. Generally, Pulse Oximetry sensors comprise emitters and detectors for at least two wavelengths of light, a red light and an infrared light. Sensor 40 and/or device 10 may also comprise an algorithm for processing or otherwise modifying the data received by the sensor (including, for example, to properly respond to movement artifacts).

According to yet another embodiment, portable monitoring device 10 comprises a power source 50. The power source may comprise one or more batteries and a power conditioner. Device 10 may also comprise an AC input that allows for charging of a rechargeable battery.

According to another embodiment, portable monitoring device 10 comprises communication circuitry, such as input 60 and/or output 70 circuitry for a wireless and/or wired connection. The communication circuitry can utilize any form of communications (including, for example, wireless, optical, or wired) and/or protocol now known or later developed (including, for example, WLAN, Wi-Fi, Internet-based communications, Bluetooth, and/or SMS, among others). Accordingly, portable monitoring device 10 may interface or communicate via any connectivity or protocol (including, for example, wired, wireless, electrical and/or optical, as described above, as well as all forms of USB and/or removable memory). Accordingly, portable monitoring device 10 may transmit information (including raw and/or processed data) to the user or the user's healthcare professional using removable memory, wireless communications, and/or wired communications.

According to another embodiment, portable monitoring device 10 comprises one or more onboard patient notification components such as a tactile alarm 80 and an audio alarm 110. This tactile or haptic feedback technology can comprise, for example, a certain noise, an electrical stimulus, and/or a motor that causes motion or vibration such that a user is notified of an alarm condition. The onboard patient notification component may also be a light alarm that flashes or otherwise notifies the user when an alarm condition is reached, or can be a light that presents a specific color to the user based on current conditions. The audio alarm may comprise a variety of audible patient notifications including voice prompts and tones.

According to another embodiment, portable monitoring device 10 comprises one or more onboard patient notification components such as a tactile alarm 80 such that the wearer of the device will feel the vibrations triggered. By this simple reminder she will learn to pay more attention to the rhythmicity of her breathing, resulting in better health.

Accordingly, device 10 may comprise a logic gate or circuit that continuously or periodically monitors and/or queries the user's data—either direct measurements or processed data—to determine whether a preprogrammed or predetermined condition has been met. For example, a user can set device 10 to create an alert when the detected heart rate or breathing rate falls outside a preprogrammed range. The user may be able to program the particular range in question, as well as the type of alarm, the dataset of measurements to be queried (within the past minute, 5 minutes, 30, minutes, etc.).

According to another embodiment, portable monitoring device 10 comprises a processor and/or circuitry 90 for data acquisition and signal processing. This is any circuitry, conversion, adaptation, modification, and/or processing component that is required to adapt the raw input (either digital or analog) into a format that can be utilized for analysis or further processing.

According to another embodiment, portable monitoring device 10 comprises onboard data storage capability 100. The onboard data storage capability 100 may be any form of data storage known or later created, and can include, for example, ROM, RAM, flash memory, and other types of non-transitory storage media. Data storage 100 can store, for example, raw data collected by the one or more sensors of device 10, either continuously or periodically. The storage may also store post-processed data for transmission or continued analysis or processing. Many other types of information can be stored in data storage 100.

Portable monitoring device 10 is preferably positioned directly on the chest or neck or otherwise proximate to the respiratory tract in order to detect respiratory and/or cardiac sounds. According to one embodiment, device 10 comprises an adhesive substrate that adheres to a surface of the chest or neck and maintains a suitable proximity of the device to the chest, neck, respiratory tract, or heart. The adhesive substrate, shown as 120 in FIG. 3, can envelope, surround, or include within all or part of the elements of the device, including but not limited to audio sensor 30 and SpO$_2$ sensor 40, among other components. Alternatively, device 10 can be part of a necklace or lanyard worn by a user, wherein the device hangs from the necklace or lanyard and is thus situated on the chest or neck area of the user. As yet another embodiment, device 10 may be incorporated into or attached to clothing worn by the user, including but not limited to a shirt, a tie, neckband, or other article of clothing worn over the torso or around the neck.

The block diagrams in FIGS. 4 and 5 are alternative schematic representations of the portable monitoring device 10. The devices comprise one or more sensors, including but not limited to Audio Sensor 30 and SpO$_2$ Sensor 40. Data collected by the sensors can be stored in data storage 100, and/or can be processed by processor 200, and/or can be analyzed by logic circuitry 210 which determines whether an alarm condition has been satisfied. If so, then alarm circuitry 220 creates an alarm as described herein. The device may also comprise communication circuitry for wired and/or wireless communication of data. These devices may also comprise one or more of the other elements described herein and otherwise within the scope of the claims and the specification.

The device in FIG. 5 also depicts a user interface 240, which can receive information from the user and communication information to the user. For example, user interface 240 can be used to set the conditions for alarm alerts. As just one example, the user can use user interface 240 to set an acceptable range for average breaths per minute, with a certain alarm resulting from measurements that fall outside the acceptable range. To accomplish this interaction, user interface 240 may be one or more buttons, or the user interface can be, for example, an audio input to receive a command from the user. To this effect, the user interface may actually be one or more of the audio sensors 30 which is adapted to recognize certain preprogrammed voice commands.

Figure 6:
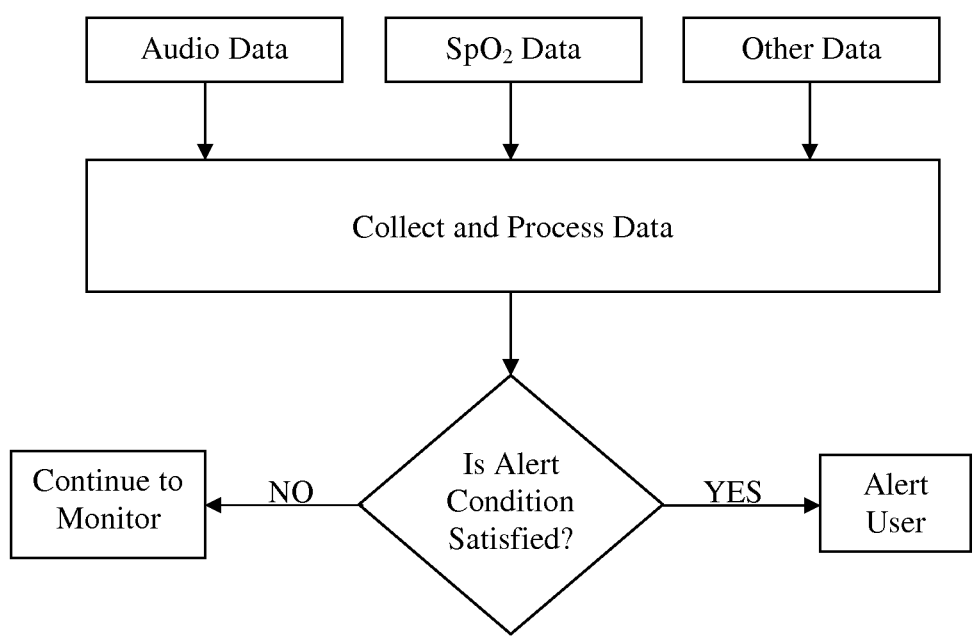
FIG. 6 is flowchart of data collection and processing according to one embodiment.

The flowchart in FIG. 6 depicts a continuous or periodic processing scheme for portable monitoring device 10. Audio Sensor 30 and SpO$_2$ Sensor 40, as well as any other sensors, collect data that is processed by the processor. The logic and/or alarm circuitry periodically or continuously monitors the sensor data—or processed data—for one or more programmed alert conditions. For example, the logic and/or alarm circuitry can monitor the user's heart rate to determine if it exceeds a certain preprogrammed value. For example, a simple logic gate can be used to determine whether the average bpm for the last minute exceeds a preprogrammed bpm. If so, then the alarm circuitry receives authorization or a request to alert the user to the existence of the alarm condition. If no alarm condition has been met, then the logic and/or alarm circuitry can continue to periodically or continuously monitor sensor and/or processed data for the alarm condition.

As will be appreciated by one skilled in the art, aspects of the present invention may be embodied as a system, method or computer program product. Accordingly, aspects of the present invention may take the form of an entirely hardware embodiment, an entirely software embodiment or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Although the present invention has been described in connection with a preferred embodiment, it should be understood that modifications, alterations, and additions can be made to the invention without departing from the scope of the invention as defined by the claims.

What is claimed is:

1. A portable monitoring device comprising:
    a housing adapted to couple to a user proximate to a portion of the user's respiratory tract, wherein a first portion of the housing faces toward the user's respiratory tract, and wherein a second portion of the housing faces away from the user's respiratory tract;
    a first audio sensor facing toward the user's respiratory tract and disposed in the first portion of the housing, wherein the first audio sensor is adapted to detect a breath sound of the user and create breath sound data;
    a second audio sensor facing away the user's respiratory tract and disposed in the second portion of the housing, wherein the second audio sensor is adapted to detect ambient noise and to create ambient sound data;
    a processor coupled to the first and second audio sensors, wherein the processor transduces the breath sound data into a modified breath sound signal which is representative of a parameter of the user's breathing, and further wherein the processor is adapted to compare the parameter of the user's breathing to a predetermined parameter threshold, wherein the processor further utilizes the ambient sound data to transduce the breath sound data into said modified breath sound signal, and further wherein the processor is configured to transduce the breath sound data into said modified breath sound signal by performing: (i) a first level analysis configured to derive one or more basic metrics from the breath sound data; and (ii) a second level analysis configured to, utilizing the one or more derived basic metrics, derive a metric providing feedback to the user or a health care professional;
    wherein the feedback to the user comprises an interactive breathing exercise algorithm when the user's breathing exceeds said predetermined parameter threshold; and
    an onboard signal generator, coupled to the processor, configured to generate a haptic signal to alert the user that said user's breathing exceeds said predetermined parameter threshold;
    wherein the generation of the haptic signal triggers a vibration of the housing on the user.

2. The portable monitoring device of claim 1, further comprising: a pulse oximetry sensor, coupled to the processor, adapted to detect a heart rate value and a blood oxygenation value.

3. The portable monitoring device of claim 1, further comprising:
    a non-transitory data storage medium adapted to store at least a portion of said breath sound data and at least a portion of said ambient sound data.

4. The portable monitoring device of claim 1, further comprising:
    a display, coupled to the processor, adapted to output data to the user.

5. The portable monitoring device of claim 1, wherein said parameter of the user's breathing is selected from the group consisting of inhalation frequency or quality, exhalation frequency or quality, breath volume, breaths per minute, and combinations thereof.

6. The portable monitoring device of claim 1, further comprising:
   a communications module, coupled to the processor, adapted to communicate data from the portable monitoring device.

7. The portable monitoring device of claim 6, wherein the communications module communicates data wirelessly.

8. The portable monitoring device of claim 1, further comprising:
   an adhesive adapted to adhere the portable monitoring device to the skin of the user.

9. The portable monitoring device of claim 1, further comprising:
   a user interface, coupled to the processor, and adapted to receive an input from the user.

10. A portable monitoring device comprising:
   a housing adapted to couple to a user proximate to the user's respiratory tract, wherein a first portion of the housing faces toward the user's respiratory tract, and wherein a second portion of the housing faces away from the user's respiratory tract;
   a first audio sensor facing toward the user's respiratory tract and disposed in the first portion of the housing, wherein the first audio sensor is adapted to detect a breath sound of the user and create breath sound data;
   a second audio sensor facing away the user's respiratory tract and disposed in the second portion of the housing, wherein the second audio sensor is adapted to detect ambient noise and to create ambient sound data;
   a pulse oximetry sensor, disposed in the housing, adapted to detect a heart rate value and a blood oxygenation value;
   a processor coupled to the first and second audio sensors and the pulse oximetry sensor, wherein the processor transduces the breath sound data into a modified breath sound signal which is representative of a parameter of the user's breathing, and further wherein the processor is adapted to compare the parameter of the user's breathing to a predetermined parameter threshold, wherein the processor further utilizes the ambient sound data to transduce the breath sound data into said modified breath sound signal, and further wherein the processor is configured to transduce the breath sound data into said modified breath sound signal by performing: (i) a first level analysis configured to derive one or more basic metrics from the breath sound data; and (ii) a second level analysis configured to, utilizing the one or more derived basic metrics, derive a metric providing feedback to the user or a health care professional;
   wherein the feedback to the user comprises an interactive breathing exercise algorithm when the user's breathing exceeds said predetermined parameter threshold;
   wherein the processor is also configured to perform an analysis of the heart rate value and the blood oxygenation value detected by the pulse oximetry sensor to detect a movement artifact;
   a non-transitory data storage medium adapted to store at least a portion of said breath sound data, at least a portion of said ambient sound data, said heart rate value, and said blood oxygenation value;
   an onboard signal generator, coupled to the processor, adapted to generate a signal to alert the user that said user's breathing exceeds said predetermined parameter threshold, or if said heart rate value or said blood oxygenation value exceeds a predetermined threshold; and
   a communications module, coupled to the processor, adapted to communicate data from the portable monitoring device.

11. The portable monitoring device of claim 10, further comprising:
   a display, coupled to the processor, adapted to output data to the user.

12. The portable monitoring device of claim 10, wherein said parameter of the user's breathing is selected from the group consisting of inhalation frequency or quality, exhalation frequency or quality, breath volume, breath flow, breaths per minute, respiratory rhythmicity, respiratory plasticity and combinations thereof.

13. The portable monitoring device of claim 10, wherein the communications module communicates data wirelessly.

14. The portable monitoring device of claim 10, further comprising:
   a user interface, coupled to the processor, and adapted to receive an input from the user.

15. A method for monitoring a health parameter of a user, the method comprising the steps of:
   providing a portable monitoring device, the device comprising: a housing adapted to couple to the user proximate to the user's respiratory tract, wherein a first portion of the housing faces toward the user's respiratory tract, and wherein a second portion of the housing faces away from the user's respiratory tract; a first audio sensor facing toward the user's respiratory tract and disposed in the first portion of the housing, wherein the first audio sensor is adapted to detect a breath sound of the user and create breath sound data; a second audio sensor facing away the user's respiratory tract and disposed in the second portion of the housing, wherein the second audio sensor is adapted to detect ambient noise and to create ambient sound data; a pulse oximetry sensor, coupled to the processor, adapted to detect a heart rate value and a blood oxygenation value; and a processor coupled to the first and second audio sensors;
   transducing, using the processor, the breath sound data and the ambient sound data into a modified breath sound signal which is representative of a health parameter of a user, comprising the steps of: (i) performing a first level analysis configured to derive one or more basic metrics from the breath sound data; and (ii) performing a second level analysis configured to, utilizing the one or more derived basic metrics, derive a metric providing feedback to the user or a health care professional;
   wherein the feedback to the user comprises an interactive breathing exercise algorithm when the user's breathing exceeds said predetermined parameter threshold;
   analyzing, using the processor, the heart rate value and the blood oxygenation value detected by the pulse oximetry sensor to detect a movement artifact;
   comparing, using the processor, the health parameter of a user to a predetermined parameter threshold; and
   generating, by an onboard signal generator coupled to the processor, a haptic signal to alert the user when said user's breathing exceeds said predetermined parameter threshold.

16. The method of claim 15, wherein said device further comprises a communications module coupled to the processor, and further comprising the step of communicating data from the portable monitoring device.

* * * * *